United States Patent
Svelto et al.

(10) Patent No.: US 10,149,837 B2
(45) Date of Patent: Dec. 11, 2018

(54) SELECTIVE AGONISTS OF BETA-ADRENERGIC TYPE 3 RECEPTORS (BAR3) AND USE THEREOF

(71) Applicants: UNIVERSITA' DEGLI STUDI DI BARI, Bari (IT); UNIVERSITA' DEGLI STUDI DELLA BASILICATA, Potenza (IT); UNIVERSITA' DEGLI STUDI DI PISA, Pisa (IT)

(72) Inventors: Maria Svelto, Bari (IT); Giuseppe Procino, Bari (IT); Monica Carmosino, Potenza (IT); Massimo Dal Monte, Pisa (IT); Paola Bagnoli, Pisa (IT)

(73) Assignees: UNIVERSITA' DEGLI STUDI DI BARI, Bari (IT); UNIVERSITA' DEGLI STUDI DELLA BASILICATA, Potenza (IT); UNIVERSITA' DEGLI STUDI DI PISA, Pisa (IT)

( * ) Notice: Subject to any disclaimer, the term of this patent is extended or adjusted under 35 U.S.C. 154(b) by 0 days.

(21) Appl. No.: 15/513,213

(22) PCT Filed: Sep. 23, 2015

(86) PCT No.: PCT/IB2015/057331
§ 371 (c)(1),
(2) Date: Mar. 22, 2017

(87) PCT Pub. No.: WO2016/046763
PCT Pub. Date: Mar. 31, 2016

(65) Prior Publication Data
US 2017/0296516 A1    Oct. 19, 2017

(30) Foreign Application Priority Data

Sep. 23, 2015   (IT) .............................. MI2014A1676

(51) Int. Cl.
*A61K 31/426*    (2006.01)

(52) U.S. Cl.
CPC .................................. *A61K 31/426* (2013.01)

(58) Field of Classification Search
CPC .................................................... A61K 31/425
See application file for complete search history.

(56) References Cited

U.S. PATENT DOCUMENTS

2006/0019954 A1    1/2006   Chen

FOREIGN PATENT DOCUMENTS

| EP | 1440969 | 7/2004 |
| WO | 20130033178 | 3/2013 |

OTHER PUBLICATIONS

International search report dated Dec. 22, 2015 for PCT/IB2015/057331.
Search Report dated Dec. 15, 2014 for Italian priority application No. MI2014A001676.

(Continued)

*Primary Examiner* — San Ming R Hui

(57) ABSTRACT

Object of the present invention is the use of selective agonists of beta-adrenergic type 3 receptors (BAR3) in the treatment of nephrogenic diabetes insipidus (NDI), in particular of X-linked nephrogenic diabetes insipidus (X-NDI).

17 Claims, 4 Drawing Sheets

(56) References Cited

OTHER PUBLICATIONS

Database WPI Week 201432 Thomson Scientific, London GB; AN 2014-F98390 XP002733730, & IN CHE 201203843 A1 Reddy's Lab Ltd Mar. 21, 2014.
Anonymous: Nephrogenic diabetes insipidus—Wikipedia, the free encyclopedia Dec. 11, 2014, XP055158426.
Barbier et al "Proinflammatory role of leptin in experimental colitis in rats Benefit of cholecystokinin-B antagonist and β3-agonist", Life Sciences, vol. 69, Issue 5, Jun. 22, 2001, pp. 567-580 (abstract).
Lenard et al "Activation of beta2- and beta3-Adrenergic Receptors Increases Brain Tryptophan". The Journal of pharmacology and experimental therapeutics 2003; 305:653-659.
Oriowo et Al.: "The selectivity in vitro of the stereoisomers of the beta-3 adrenoceptor agonist brl 37344". The Journal of pharmacology and experimental therapeutics. 1996;277:22-27.
Strosberg AD, Pietri-Rouxel F: Function and regulation of the beta 3-adrenoceptor. Trends in pharmacological sciences 1996;17:373-381;(abstract).
Herschorn S, Barkin J, Castro-Diaz D, Frankel JM, Espuna-Pons M, Gousse AE, Stolzel M, Martin N, Gunther A, Van Kerrebroeck P: A phase iii, randomized, double-blind, parallel-group, placebo-controlled, multicentre study to assess the efficacy and safety of the beta(3) adrenoceptor agonist, mirabegron, in patients with symptoms of overactive bladder. Urology 2013;82:313-320;(abstract).
Krauwinkel W, van Dijk J, Schaddelee M, Eltink C, Meijer J, Strabach G, van Marie S, Kerbusch V, van Gelderen M: Pharmacokinetic properties of mirabegron, a beta3-adrenoceptor agonist: Results from two phase i, randomized, multiple-dose studies in healthy young and elderly men and women. Clinical therapeutics 2012;34:2144-2160; (abstract).
Takasu T, Ukai M, Sato S, Matsui T, Nagase I, Maruyama T, Sasamata M, Miyata K, Uchida H, Yamaguchi O: Effect of (r)-2-(2-aminothiazol-4-yl)-4'-{2-[(2-hydroxy-2-phenyl)amino]ethyl} acetanilide (ym178), a novel selective beta3-adrenoceptor agonist, on bladder function. The Journal of pharmacology and experimental therapeutics 2007;321:642-647.
Takusagawa S, van Lier JJ, Suzuki K, Nagata M, Meijer J, Krauwinkel W, Schaddelee M, Sekiguchi M, Miyashita A, Iwatsubo T, van Gelderen M, Usui T: Absorption, metabolism and excretion of [(14)c]mirabegron (ym178), a potent and selective beta(3)-adrenoceptor agonist, after oral administration to healthy male volunteers. Drug metabolism and disposition: the biological fate of chemicals 2012;40:815-824;(abstract).
Yamaguchi O, Marui E, Kakizaki H, Homma Y, Igawa Y, Takeda M, Nishizawa O, Gotoh M, Yoshida M, Yokoyama O, Seki N, Ikeda Y, Ohkawa S: Phase iii, randomised, double-blind, placebo-controlled study of the beta3-adrenoceptor agonist mirabegron, 50 mg once daily, in Japanese patients with overactive bladder. BJU international 2014;113:951-960;Abstract.

SELECTIVE AGONISTS OF BETA-ADRENERGIC TYPE 3 RECEPTORS (BAR3) AND USE THEREOF

RELATED APPLICATION

This application is the U.S. national phase application of international application No. PCT/IB2015/057331, filed 23 Sep. 2015, which designates the U.S. and claims priority to Italian application MI2014A001676 filed 26 Sep. 2014, the contents of each of which are hereby incorporated by reference as if set forth in their entireties.

TECHNICAL FIELD

Object of the present invention is the use of known compounds, for the treatment of X-linked nephrogenic diabetes insipidus.

The concentration process of urine, by which the hydrosaline balance of the whole organism strictly depends, is carried out in the kidney, in the renal tubule thanks to a concerted mechanism of resorption of solutes and water from the lumen of the tubule to the blood. This process allows the 180 liters of pro-urine formed each day in humans to be reabsorbed by determining the excretion of about two liters of urine containing waste molecules. The regulation of this process of resorption is entrusted to the antidiuretic vasopressin (AVP) hormone, which regulates the activity and abundance of ionic carriers (symporter NKCC2) in the thick ascending limb (TAL) of the renal loop, and water channels (aquaporins, AQP2-AQP3) in the renal collecting duct (CD). AVP links its receptor (AVPR2) located on the cell surface of these limbs and triggers an intracellular signaling mediated by the second messenger cAMP, that is increasing the NKCC2 activity and both AQP2 and AQP3 expressions. In subjects in whom mutations of the receptor prevent its action, the salt and water resorption is compromised. It follows that such subjects produce enormous quantities of urine with low specific weight and are constantly threatened by dehydration (lack of water in the organism) and hypernatremia, i.e. the increase of the sodium rate in the blood. The just described symptoms define a condition that is rare and still missing a decisive and targeted drug treatment, known as X-linked nephrogenic diabetes insipidus (X-NDI).

The nephrogenic diabetes insipidus (NDI) of X-linked type is a rare condition that affects more frequently males than females, due to the mode of genetic inheritance. 90% of the reported cases of nephrogenic diabetes insipidus are in fact of X-linked type.

One of the world's leading experts, Dr. Daniel Bichet, estimated that 4 individuals per million are affected with X-linked NDI. All these subjects could benefit from a therapy allowing drastically reducing, if not completely eliminating, negative effects of the disease without showing side effects currently strictly related to the use of currently used therapies.

At present, there is no cure for the condition known as X-NDI or also for the NDI only. In patients affected with such a disease, the symptomatology associated with NDI is kept under control by assuring their continuous hydration, by providing them a hyposodic diet and subjecting them to treatment with diuretics based on thiazide, alone or in combination with inhibitors of the prostaglandin synthesis or potassium-sparing diuretics, so as to reduce the volume of produced urine.

Thiazide diuretics, used for the treatment of NDI, decrease the fraction of sodium reabsorbed in the distal tubule, causing hypovolemia, i.e. the decrease of the volume of circulating blood. In order to compensate this situation, the renin-angiotensin-aldosterone system (RAAS) is activated which, by enhancing the aldosterone blood levels, determines a higher sodium resorption in the proximal tubule. As the sodium resorption in the proximal tubule is together with an iso-osmotic transport of water, this increases the total amount of water reabsorbed in the proximal nephron and, as a consequence, reduces the volume of urine arriving to the distal nephron. The volume of urine produced by patients under therapy of currently known type is thus halved.

Unfortunately however, the administration of such molecules, while improving the patient symptomatology, shows important side effects.

The thiazide is able to reduce the polyuria (i.e. the formation and excretion of excessive amount of urine in the absence of a simultaneous increase of liquid intake) but, at the same time, can deplete and thus significantly reduce the deposits of potassium in the organism. The loss of potassium is a condition very dangerous in itself for the organism and must be constantly kept under control by integration of potassium or therapy based on amiloride.

Among inhibitors of the prostaglandin synthesis, indomethacin is one of the most used in the treatment of NDI. However it is a non-steroidal anti-inflammatory drug which can cause migraine, dizziness and can increase the risk of gastrointestinal disorders. If administered in the first year of life, it can increase the risk of renal disease.

Furthermore, in the NDI of X-linked type or linked to chromosome X as defined above, indomethacin and thiazide cause a decrease in the glomerular filtration rate (GFR), thus determining an increase of the risk of nephropathy.

Using instead nonspecific inhibitors of the cyclooxygenases for the therapy of NDI can imply significant side effects on the cardiac function.

In patients subjected to the just described therapy, the volume of urine produced and secreted by the organism is significantly reduced, but however it does not fall below 4-12 liters/day.

SUMMARY AND OBJECTS OF THE INVENTION

Thus, object of the present invention is to provide alternative substances that are used in the treatment of nephrogenic diabetes insipidus (NDI), in particular of X-linked nephrogenic diabetes insipidus (X-NDI), which allow restoring normal levels of aquaporin 2 (AQP2) on the luminal membrane of the main cells of the renal collecting duct.

Another object of the present invention is to provide alternative substances that are used in the treatment of nephrogenic diabetes insipidus (NDI), in particular of X-linked nephrogenic diabetes insipidus (X-NDI), which allow effectively correcting polyuria that affects patients suffering from NDI.

Further object of the invention is to provide alternative substances that are used in the treatment of nephrogenic diabetes insipidus (NDI), in particular of X-linked nephrogenic diabetes insipidus (X-NDI), which allow directly correcting the defect in the protein AQP2 transport which is the basis of the pathological phenotype.

Still object of the invention is to provide alternative substances that are used in the treatment of nephrogenic diabetes insipidus (NDI), in particular of X-linked nephrogenic diabetes insipidus (X-NDI), that allow limiting, if not even eliminating, systemic effects connected to currently available drug treatments according to known art.

Still object of the present invention is to provide alternative substances that are used in the treatment of nephrogenic diabetes insipidus (NDI), in particular of X-linked nephrogenic diabetes insipidus (X-NDI), which determine the remission of the X-NDI phenotype and simultaneously show mild and transient side effects.

These and other objects, that will be better clarified below, are obtained by the present invention, which has the object of using selective agonists of beta-adrenergic type 3 receptors (BAR3) in the treatment of nephrogenic diabetes insipidus (NDI), in particular of X-linked nephrogenic diabetes insipidus (X-NDI).

DESCRIPTION OF EMBODIMENTS OF THE INVENTION

Figure 1:
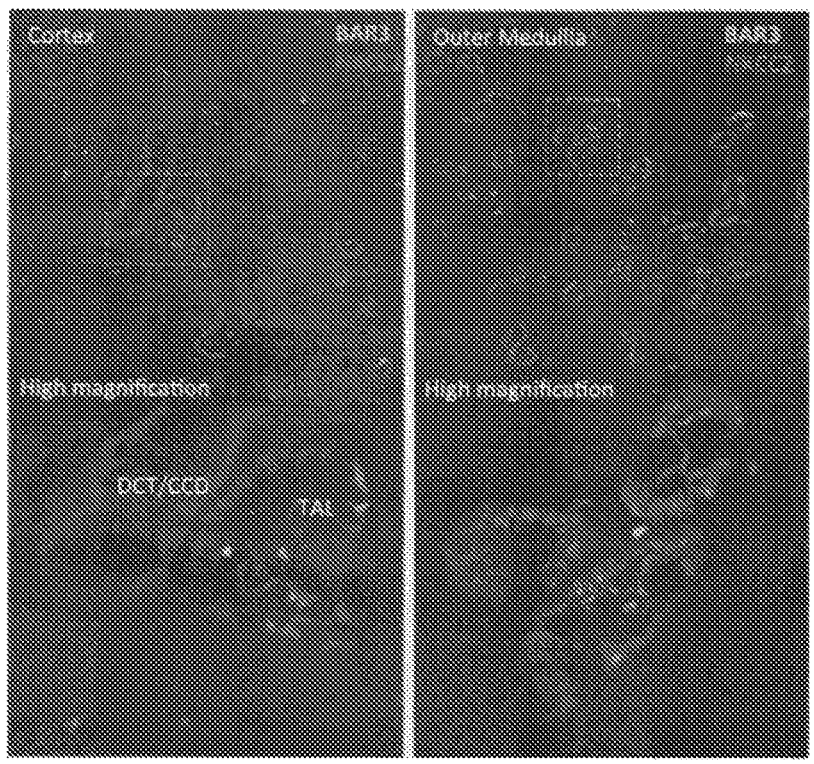
FIGS. 1-3 represent histological samples that show embodiments of various experimental results of embodiments of the invention.

Thus, the present invention consists in using selective agonists of beta-adrenergic type 3 receptors (BAR3) in the cells of renal collecting duct in order to correct a rare genetic human condition such as nephrogenic diabetes insipidus (NDI), in particular X-linked nephrogenic diabetes insipidus (X-NDI).

In particular, being such BAR3 receptors expressed in cells of collecting duct and thick ascending limb of the loop of Henle, and being the intracellular signal cascade activated by them mediated by cAMP, it is possible to activate such a transduction pathway also in cells in which this pathway is blocked due to mutations of the receptor for vasopressin AVPR2. Such mutations are responsible for the rare condition, missing a cure, known as X-linked nephrogenic diabetes insipidus. Surprisingly it has been seen that the stimulation of BAR3 can short-circuit the defect.

The use of selective agonists of BAR3, among which the BRL37344 compound suitable for the use on rodents, and YM-178 compound already tested in humans, leads to the healing of such a condition.

According to the present invention surprisingly it has been seen that, in the murine renal tubule, the cells of the thick ascending limb (TAL) of the loop and of cortical collecting duct (CCD) express beta-adrenergic type 3 receptors (BAR3). These receptors act with the same mechanism of intracellular transduction of signal activated by the receptor for vasopressin AVPR2. It has been seen that, by stimulating the BAR3 receptors also in subjects having the above described condition of X-linked nephrogenic diabetes insipidus (X-NDI), it is possible to by-pass the inactivation of the AVPR2 receptor and, totally or in part, restore a normal phenotype.

The selective agonist of BAR3 in mice is the BRL37344 molecule, the latter being known for example on the basis of the following bibliographical references:

Barbier M, Attoub S, Joubert M, Bado A, Laboisse C, Cherbut C, Galmiche J P: Proinflammatory role of leptin in experimental colitis in rats benefit of cholecystokinin-b antagonist and beta3-agonist. Life sciences 2001;69:567-580;

Lenard N R, Gettys T W, Dunn A J: Activation of beta2- and beta3-adrenergic receptors increases brain tryptophan. The Journal of pharmacology and experimental therapeutics 2003;305:653-659;

Oriowo M A, Chapman H, Kirkham D M, Sennitt M V, Ruffolo R R, Jr., Cawthorne M A: The selectivity in vitro of the stereoisomers of the beta-3 adrenoceptor agonist brl 37344. The Journal of pharmacology and experimental therapeutics 1996;277:22-27;

Strosberg A D, Pietri-Rouxel F: Function and regulation of the beta 3-adrenoceptor. Trends in pharmacological sciences 1996;17:373-381;

commercially available for purposes of scientific research. BRL37344 is also known as (±)-(R*,R*)-[4-[2-[[2-(3-Chlorophenyl)-2-hydroxyethyl]amino] propyl] phenoxy] acetic acid sodium hydrate, and is available in the market for example by Sigma-Aldrich at the time of filing of the present application.

The corresponding selective for humans is the compound named YM-178 (current commercial name Mirabegron), known for example on the basis of the following bibliographical references:

Herschorn S, Barkin J, Castro-Diaz D, Frankel J M, Espuna-Pons M, Gousse A E, Stolzel M, Martin N, Gunther A, Van Kerrebroeck P: A phase iii, randomized, double-blind, parallel-group, placebo-controlled, multicentre study to assess the efficacy and safety of the beta(3) adrenoceptor agonist, mirabegron, in patients with symptoms of overactive bladder. Urology 2013;82:313-320;

Krauwinkel W, van Dijk J, Schaddelee M, Eltink C, Meijer J, Strabach G, van Marle S, Kerbusch V, van Gelderen M: Pharmacokinetic properties of mirabegron, a beta3-adrenoceptor agonist: Results from two phase i, randomized, multiple-dose studies in healthy young and elderly men and women. Clinical therapeutics 2012;34:2144-2160;

Takasu T, Ukai M, Sato S, Matsui T, Nagase I, Maruyama T, Sasamata M, Miyata K, Uchida H, Yamaguchi O: Effect of (r)-2-(2-aminothiazol-4-yl)-4'-{2-[(2-hydroxy-2-phenylethyl) amino]ethyl} acetanilide (ym178), a novel selective beta3-adrenoceptor agonist, on bladder function. The Journal of pharmacology and experimental therapeutics 2007;321:642-647;

Takusagawa S, van Lier J J, Suzuki K, Nagata M, Meijer J, Krauwinkel W, Schaddelee M, Sekiguchi M, Miyashita A, Iwatsubo T, van Gelderen M, Usui T: Absorption, metabolism and excretion of [(14)c]mirabegron (ym178), a potent and selective beta(3)-adrenoceptor agonist, after oral administration to healthy male volunteers. Drug metabolism and disposition: the biological fate of chemicals 2012;40:815-824;

Yamaguchi O, Marui E, Kakizaki H, Homma Y, Igawa Y, Takeda M, Nishizawa O, Gotoh M, Yoshida M, Yokoyama O, Seki N, Ikeda Y, Ohkawa S: Phase iii, randomised, double-blind, placebo-controlled study of the beta3-adrenoceptor agonist mirabegron, 50 mg once daily, in japanese patients with overactive bladder. BJU international 2014;113:951-960;

and already currently available in the market, for the use in the clinical field for the healing of overactive bladder, marketed as Mirabegron and otherwise identified as 2-(2-Amino-1, 3-thiazol-4-yl)-N-[4-(2-{[(2R)-2-hydroxy-2-phenylethyl]amino}ethyl)phenyl]acetamide.

Characteristics of this novel pharmacological approach for the nephrogenic diabetes insipidus are, for example, the possibility of restoring normal levels of AQP2 on the luminal membrane of the main cells of renal collecting duct by using agonists of BAR3 receptors. As already stated, a product agonist of BAR3 receptors already available on the market for a different use, is called YM-178/Mirabegron.

Once expressed on the plasmatic membrane, AQP2 will determine the resorption of water, by correcting the polyuria that is affecting the patients suffering from NDI.

Furthermore, the stimulation of TAL should increase the resorption of solutes by raising the osmolarity of the renal medulla, which is the driving force for the resorption of water. This kind of approach in the treatment of X-linked nephrogenic diabetes insipidus is completely innovative, in that it is directly aimed at correcting the defect in the transport of the protein AQP2 which is the basis of the pathological phenotype. Aim of pharmacological therapy currently in use for the treatment of NDI is not the restoration of the membrane expression of AQP2 but rather the increase of the hydric resorption in the proximal tubule. Another advantage denoted by the present invention based on the stimulation of the BAR3, is in stimulating a receptor normally present on the surface of the same cells that express the receptor for vasopressin AVPR2. Due to the limited distribution of BAR3 in other tissues and organs, further advantage of the invention is represented by modest, if not null, adverse systemic effects following such drug treatment.

In this perspective the BAR3 agonists (for example BRL37344 selective for mice, YM-178 specific for humans and their derivatives and related compounds) are able to achieve two targets: 1) determining the remission of X-NDI phenotype and 2) showing mild and transient side effects. Ex vivo and in vivo evidences clearly denote that, for example, BRL37344 is able to increase the apical levels of AQP2 with an effect comparable to that produced by vasopressin.

A further advantage of the present invention is that Mirabegron is an already approved drug (2012) by EMA and FDA for use on humans. Thus the pharmacodynamics, pharmacokinetics, bioavailability, appropriate dosage and side effects are known. Mirabegron is currently indicated in managing the overactive bladder, for the relief of symptoms associated with the urination: urge urinary incontinence, urinary urgency and increased frequency of urination.

Also object of the present invention is the use of the pharmaceutical compositions comprising the selective agonist compounds of beta-adrenergic type 3 receptors (BAR3) to correct a rare genetic human condition such as nephrogenic diabetes insipidus (NDI), in particular the X-linked nephrogenic diabetes insipidus (X-NDI). Such pharmaceutical compositions, comprising pharmacologically acceptable additives and excipients, are advantageously administered, still according to the invention, at a dosage between 10 mg and 100 mg, in particular at a dosage of 25 mg and 50 mg.

The preferred administration route, according to the finding, is the oral route.

The following experimental evidences are reported as further support of the present invention.

The experimental results are together with the attached Figures.

FIG. 1 shows that in the cortex and in the renal outer medulla, BAR3 (in green) stains the basolateral membrane of tubular cells expressing on the apical side the co-carrier and NKCC2 (in red), the latter being selectively expressed in the thick ascending limb (TAL) of the tubular loop. By using another marker of TAL, protein Tamm-horsfall (not shown in the figure), overlapping results have been obtained.

The tubules positive for BAR3 and negative for NKCC2 are distal convoluted tubules (DCT) or cortical collecting ducts (CCD), as depicted in the following figures.

Figure 2:
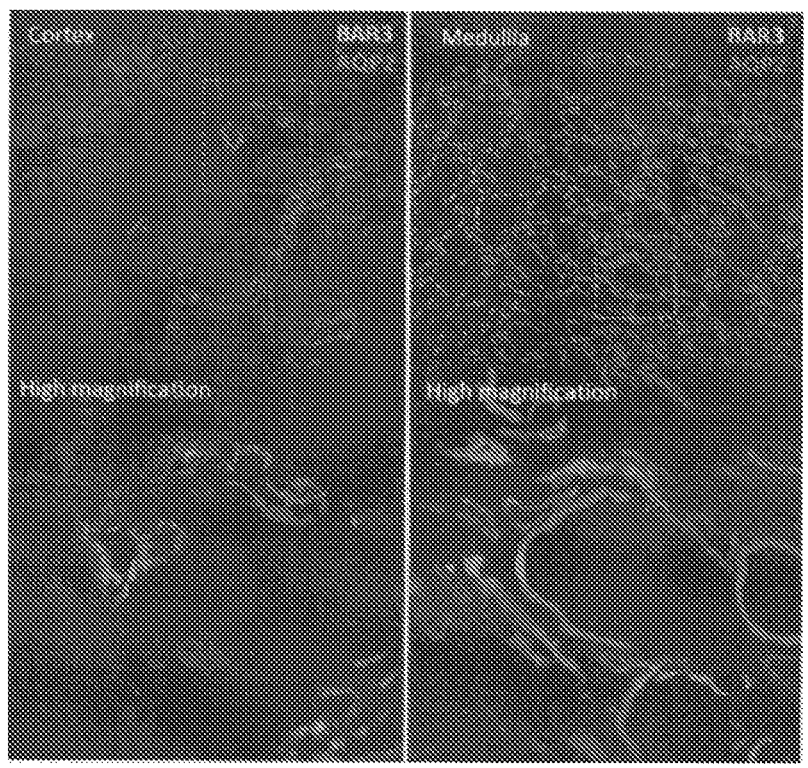

FIG. 2 shows that, in the renal cortex, BAR3 (green) and AQP2 (red) stain the same cells on opposite domains of the membrane. In the medulla, BAR3 is not located in the collecting ducts. Analogous results are obtained by the co-marking of BAR3 with the urea carrier sensitive to vasopressin (UTA-1, data not shown in the figure).

Figure 3:
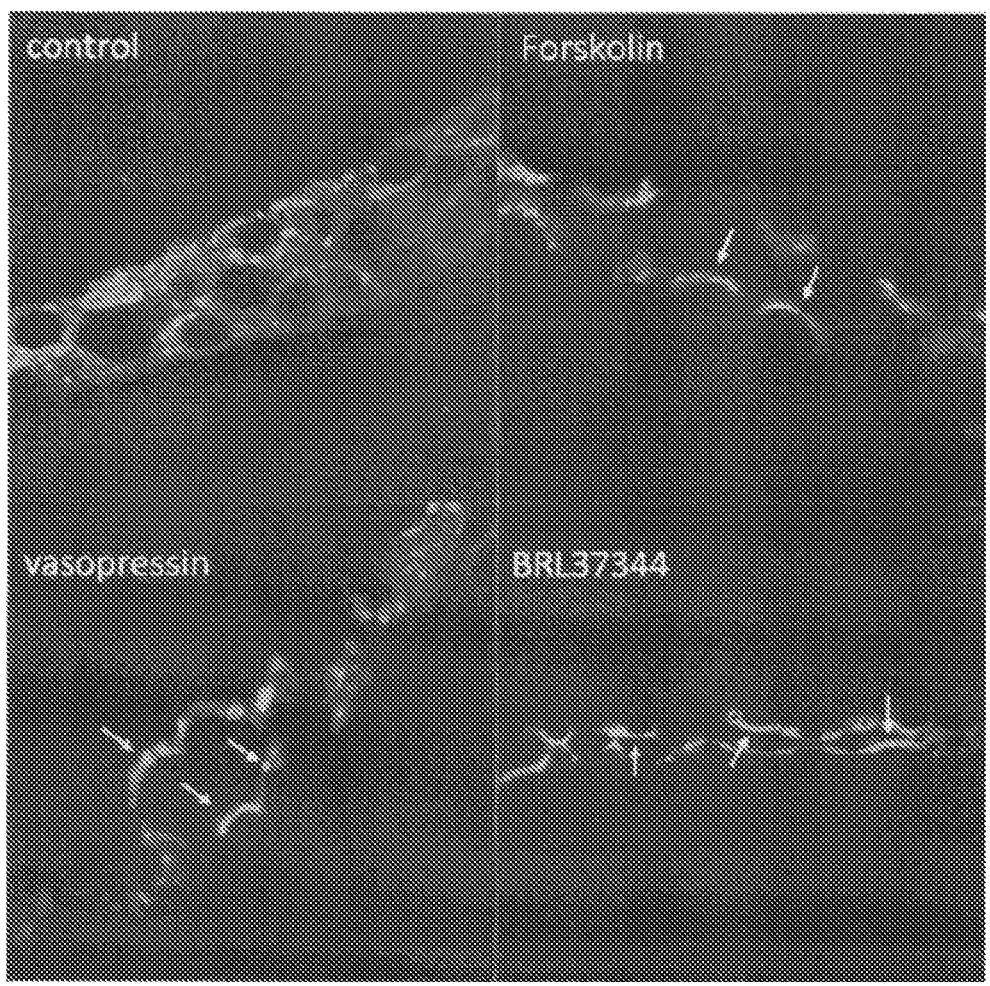

FIG. 3 shows that, in renal tissue of mice, AQP2 is located in intracellular vesicles in control conditions (ctr). The treatment with forskolin of slices of tissue raises the levels of cAMP and makes the AQP2 exocitated on the apical membrane (see white arrows). Vasopressin, the physiological ligand of AVPR2, translocates AQP2 on the apical membrane of the tubular cells. The selective agonist of BAR3 receptors of mice (BRL37344) determines an effect comparable to that of vasopressin.

Figure 4:
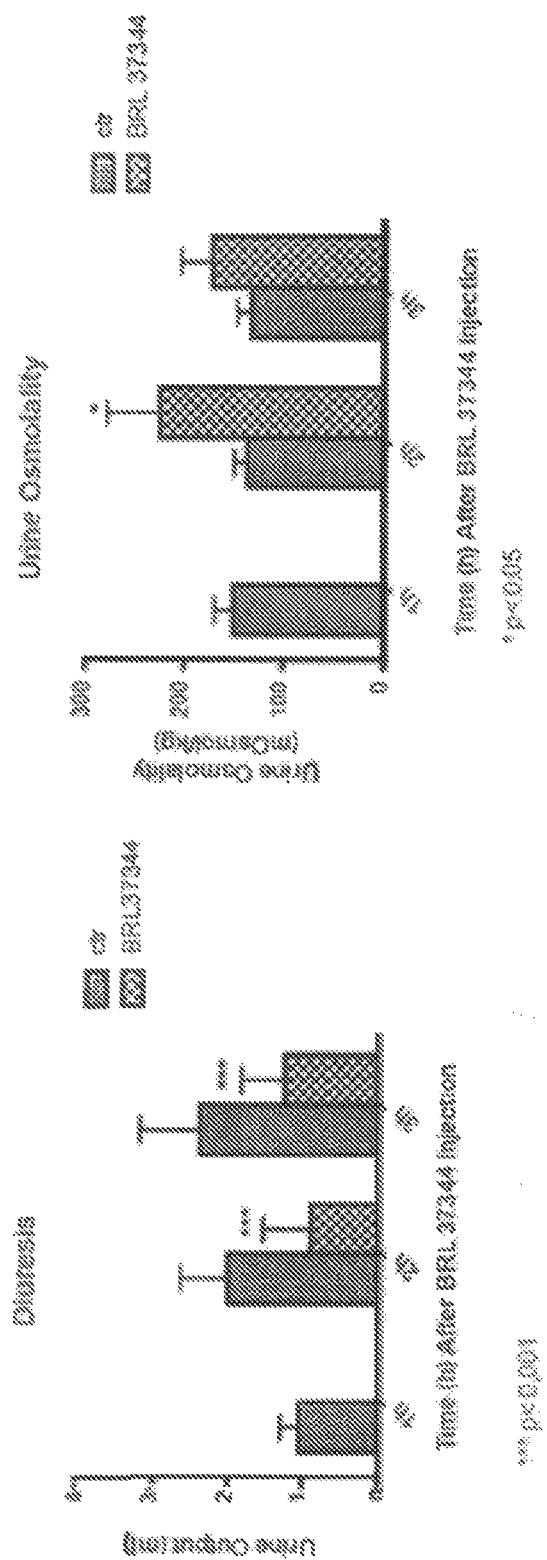
FIG. 4 shows two bar graphs illustrating the effect of the injection of BRL37344 on diuresis and urine osmolality in conditional knockout mice for AVPR2.

FIG. 4 shows the effect of the injection of BRL37344 on diuresis and urine osmolality in conditional knockout mice for AVPR2, affected by X-linked nephrogenic diabetes insipidus. At one hour from the injection of the compound, the diuresis of the treated mice is set to zero compared to control animals. At the second hour the diuresis of the treated animals is drastically reduced and urine osmolality significantly increases. At the end of the third hour from the treatment, the diuresis of the treated animals is still drastically reduced whilst osmolality shows a tendency to increase although not statistically significant.

BAR3 receptors with selective markers of specific portions of the renal tubule have been co-localized, in sections of kidney of mice, by indirect immunofluorescence and scanning by confocal microscopy of semi-thin sections (5 µM) of kidney of mice. The obtained results can be summarized as follows:

BAR3 is NOT expressed in positive cells for the marker of the proximal tubule and of the thin descending limb (TDL) of the renal loop aquaporin 1 (AQP1, data not shown)

BAR3 is NOT expressed in positive cells for the marker of the endothelium vessel CD31 (data not shown)

BAR3 is expressed on the basolateral membrane of positive cells for NKCC2, the marker of TAL (as shown in FIG. 1)

BAR3 is expressed on the basolateral membrane of positive cells for NCC carrier selectively expressed in the distal convoluted tubule (DCT, data not shown in the figure).

BAR3 is expressed on the basolateral membrane of the tubular cells expressing aquaporin 2 (AQP2) on the apical side in the collecting duct (see FIG. 2).

The expression of BAR3 in the kidney of mice has been further confirmed also by immunoblotting experiments (not shown in the figures).

According to the present invention, it has been seen that the stimulation of the receptors with the selective analogous BRL37344 stimulates the membrane expression of AQP2 on sections of vital renal tissue of mice.

By the technique of "kidney slices", thin slices of vital tissue from murine C57BL-6 kidneys have been obtained which, maintained in culture medium and appropriate atmosphere, have been stimulated with agonists able to increase the intracellular levels of cAMP (forskolin and vasopressin) and with the agonist of murine BRL37344 BAR3. After 45 minutes of stimulation the tissues have been fixed, marked for AQP2 and observed by confocal laser scanning.

The results, showed in FIG. 3, highlight that BRL37344, as much as vasopressin and forskolin, determines a repositioning of the marking of AQP2 on the apical membrane. The results denote that, in the cortical collecting duct, the stimulation of BAR3 produces an effect comparable to that of vasopressin in terms of apical expression of AQP2.

Still according to the present invention, in vivo, in the animal model of nephrogenic diabetes insipidus (X-NDI), the infusion with BRL37344 determines a drastic reduction of diuresis together with an increase of urine osmolality.

In the mouse affected by nephrogenic diabetes insipidus (X-NDI) for conditional deletion of the AVPR2 receptor, the compound BRL37344 has been administered by intraperitoneal injection at the dosage of 0.6 mg/Kg. Five animals received the compound whereas as many control animals received the vehicle only (physiological saline). The cumulative diuresis has been measured in metabolic cage in both animal groups.

The results, showed in FIG. 4, denote that at the end of the first hour after the injection, the diuresis of the treated group was set to zero in contrast to the control group. At the second hour after the injection, the diuresis in the treated group was statistically reduced compared to the control group. At the end of the third hour the cumulative diuresis of the treated group still remained statistically lower than that of the control group. The values of urine osmolality, in the treated group at the second hour after the injection of the compound, significantly increased. At the third hour, the osmolality of urine in the treated group was on average higher although not statistically different from that of the control group. The data obtained are in line with a transient effect induced by the stimulation of the renal BAR3 receptors by BRL37344.

The invention claimed is:

1. A method for treating nephrogenic diabetes insipidus comprising administering a selective agonist compound of beta-adrenergic type 3 receptors.

2. The method according to claim 1, wherein said treating comprises treating X-linked nephrogenic diabetes insipidus type.

3. The method according to claim 1, wherein said selective agonist compound of beta-adrenergic type 3 receptors is 2-(2-amino-1,3-thiazol-4-yl)-N-[4-(2-{[(2R)-2-hydroxy-2-phenylethyl]amino}ethyl)phenyl]acetamide.

4. A method for treating nephrogenic diabetes insipidus comprising administering a pharmaceutical composition comprising a selective agonist compound of beta-adrenergic type 3 receptors, along with pharmaceutically acceptable excipients and/or additives.

5. The method according to claim 4, wherein said selective agonist compound is 2-(2-amino-1,3-thiazol-4-yl)-N-[4-(2-{[(2R)-2-hydroxy-2-phenylethyl]amino}ethyl)phenyl]acetamide.

6. The method according to claim 4, wherein said pharmaceutical composition comprises 10 mg to 100 mg of 2-(2-amino-1,3-thiazol-4-yl)-N-[4-(2-{[(2R)-2-hydroxy-2-phenylethyl]amino}ethyl)phenyl]acetamide.

7. The method according to claim 6, wherein said pharmaceutical composition comprises 25 mg of 2-(2-amino-1,3-thiazol-4-yl)-N-[4-(2-{[(2R)-2-hydroxy-2-phenylethyl]amino}ethyl)phenyl]acetamide.

8. The method according to claim 6, wherein said pharmaceutical composition comprises 50 mg of 2-(2-amino-1,3-thiazol-4-yl)-N-[4-(2-{[(2R)-2-hydroxy-2-phenylethyl]amino}ethyl)phenyl]acetamide.

9. The method according to claim 6, wherein said treating comprises treating X-linked nephrogenic diabetes insipidus type.

10. A method for treatment of nephrogenic diabetes insipidus, said method comprising administering, to a subject in need thereof, an effective amount of a selective agonist compound of beta-adrenergic type 3 receptors.

11. The method according to claim 10, wherein said selective agonist compound of beta-adrenergic type 3 receptors is 2-(2-amino-1,3-thiazol-4-yl)-N-[4-(2-{[(2R)-2-hydroxy-2-phenylethyl]amino}ethyl)phenyl]acetamide.

12. A method for treatment of nephrogenic diabetes insipidus, said method comprising administering, to a subject in need thereof, a pharmaceutical composition comprising a selective agonist compound of beta-adrenergic type 3 receptors, along with pharmaceutically acceptable excipients and/or additives.

13. The method according to claim 12, wherein said selective agonist compound of beta-adrenergic type 3 receptors is 2-(2-amino-1,3-thiazol-4-yl)-N-[4-(2-{[(2R)-2-hydroxy-2-phenylethyl]amino}ethyl)phenyl]acetamide.

14. The method according to claim 12, wherein said pharmaceutical composition comprises 10 mg to 100 mg of 2-(2-amino-1,3-thiazol-4-yl)-N-[4-(2-{[(2R)-2-hydroxy-2-phenylethyl]amino}ethyl)phenyl]acetamide.

15. The method according to claim 14, wherein said pharmaceutical composition comprises 25 mg of 2-(2-amino-1,3-thiazol-4-yl)-N-[4-(2-{[(2R)-2-hydroxy-2-phenylethyl]amino}ethyl)phenyl]acetamide.

16. The method according to claim 14, wherein said pharmaceutical composition comprises 50 mg of 2-(2-amino-1,3-thiazol-4-yl)-N-[4-(2-{[(2R)-2-hydroxy-2-phenylethyl]amino}ethyl)phenyl]acetamide.

17. The method according to claim 12, wherein said administering comprises treating said subject for X-linked nephrogenic diabetes insipidus type.

* * * * *